United States Patent [19]
Brendler et al.

[11] Patent Number: 6,067,343
[45] Date of Patent: May 23, 2000

[54] X-RAY DEVICE INCLUDING A PRIMARY DIAPHRAGM DEVICE

[75] Inventors: Joachim Brendler, Hamburg; Horst Allmendinger, Elmshorn, both of Germany

[73] Assignee: U.S. Philips Corporation, New York, N.Y.

[21] Appl. No.: 09/009,746

[22] Filed: Jan. 20, 1998

[30] Foreign Application Priority Data

Jan. 27, 1997 [DE] Germany .......................... 197 02 739

[51] Int. Cl.$^7$ ...................................................... H05G 1/36
[52] U.S. Cl. .......................................... 378/98.7; 378/108
[58] Field of Search .............................. 378/96, 97, 98.3, 378/98.7, 108, 109, 111, 151, 152

[56] References Cited

U.S. PATENT DOCUMENTS

| | | | |
|---|---|---|---|
| 3,995,161 | 11/1976 | Lux | 250/416 |
| 4,573,183 | 2/1986 | Relihan | 378/108 |
| 5,260,984 | 11/1993 | Horbaschek | 378/150 |
| 5,287,396 | 2/1994 | Stegehuis | 378/98.2 |
| 5,396,531 | 3/1995 | Hartley | 378/108 |

FOREIGN PATENT DOCUMENTS

3006774A1  3/1981  Germany .

*Primary Examiner*—David P. Porta
*Attorney, Agent, or Firm*—Dwight H. Renfrew, Jr.

[57] ABSTRACT

The invention relates to an X-ray device which includes a primary diaphragm device (3) for limiting the X-ray beam and a control circuit (10) for automatic exposure control, which control circuit includes a detector (9) with at least one measuring field (31) which measures the X-ray dose rate. Whereas in the case of customary exposure control systems the X-ray dose is increased when the radiation beam is strongly limited so that parts of the measuring field (31) are not exposed, which could lead to overexposed X-ray images, the X-ray device according to the invention is provided with means (12, 14, 15, 16, 17) for determining a correction value (K) which is dependent on the dimensions of the exposed area (33) of the measuring field (31) and acts on the control circuit (10) in such a manner that an increase of the X-ray dose is even avoided in the case of a partly non-exposed measuring field (31).

20 Claims, 1 Drawing Sheet

X-RAY DEVICE INCLUDING A PRIMARY DIAPHRAGM DEVICE

BACKGROUND OF THE INVENTION

1. Field of the Invention

The invention relates to an X-ray device, including an X-ray source for emitting an X-ray beam, an X-ray image converter for detecting X-rays and for forming an X-ray image, a primary diaphragm device which, in order to limit the X-ray beam, is arranged between a radiation source and an object to be examined, and a control circuit for automatic exposure control, including a detector with at least one measuring field measuring the X-ray dose rate.

2. Description of Related Art

An X-ray device of this kind is known from DE-A 30 06 774. The control circuit thereof includes an adder which superposes two memory values on a reference value, the first memory value incorporating the dependency of the conversion factor of an X-ray image intensifier, used as the X-ray image converter, on the electrode voltage whereas the second memory value incorporates the dependency of the background (the residual brightness) of the X-ray image intensifier on the aperture of the primary diaphragm device which determines the image format. Measurement values for the automatic exposure control, falsified by the X-ray image intensifier, are thus corrected.

The area of diagnostic interest in the X-ray image should have a given mean density. The measuring field of the detector is made to register with this area of interest, and during the exposure the already applied X-ray dose is continuously measured in this measuring field by measurement of the X-ray dose rate. When a predetermined X-ray dose is reached, corresponding to a mean density, the automatic exposure control switches off the X-rays.

In order to adapt the dimensions of the area traversed by the X-ray beam to the medical requirements and to reduce, if necessary, the contrast-degrading effects of scattered radiation, a primary diaphragm device for limiting the X-ray beam is arranged between the X-ray source and an object to be examined, for example a patient. However, if limiting is so extensive, that is to say if the diaphragm aperture is made so small, that parts of the measuring field are masked by the shutters of the primary diaphragm device so that these parts are no longer exposed, overexposed X-ray images will be obtained when the conventional exposure control system is employed. This is because the detector measures the dose in the entire measuring field by averaging, even when areas of the measuring field are masked by the shutters so that they are not exposed. Therefore, the dose averaged across the entire measuring field in the case of extensive limiting is less than the dose obtained in the exposed area of the measuring field. The conventional automatic exposure control then increases the X-ray dose until the predetermined X-ray dose is reached. This often results in overexposed X-ray images, in which important image information is lost, and also leads to an increased dose for the patient.

SUMMARY OF THE INVENTION

Therefore, it is an object of the invention to provide an X-ray of the device of the kind set forth which produces X-ray images having an improved image quality.

Using an X-ray device of the kind set forth, this object is achieved in that there are provided means for determining a correction value which influences the control circuit and is dependent on the dimensions of the exposed area of the measuring field, and for influencing the control circuit in such a manner that the X-ray dose remains substantially the same even when parts of the measuring field are not exposed.

Thus, the control directly takes into account any non-exposed parts of the measuring field, because the value of the aperture of the primary diaphragm device drops below a limit value. In that case an intervention by means of the correction value takes place directly in the control circuit in order to prevent the formation of overexposed X-ray images in which important image information is missing. Control then takes place in such a manner that the X-ray dose is kept substantially constant in the case of a small primary diaphragm aperture (and a partly non-exposed measuring field) and overall is approximately equal to that in the case of a large primary diaphragm aperture (and a completely exposed measuring field). This is contrary to the customary control where the X-ray dose is substantially increased when the primary diaphragm aperture is smaller. The invention thus prevents an increase of the radiation dose in the case of stronger beam limiting.

The control circuit in an embodiment of the X-ray device according to the invention includes means for determining a dose actual value, a dose reference value and a control signal by comparison of the dose actual value with the dose reference value for controlling the X-ray source. In accordance with the invention, this control circuit can be influenced by means of the correction value in such a manner that in the case of partial masking of the measuring field because of a small primary diaphragm aperture the dose reference value is reduced as from a predetermined dose standard reference value and/or the dose actual value detected by the detector in the measuring field is increased. The dose reference values can then be stored in a memory and hence be predetermined or be selected or determined in dependence on different settings of the X-ray device, for example the distance between the X-ray source and the X-ray image converter and the magnification factor of the X-ray image converter. The calculated control signal serves to control the X-ray source or an X-ray generator by influencing the tube current, the tube voltage and/or the exposure time.

The means for determining the correction value in a further embodiment of the X-ray device according to the invention, include an arithmetic unit for determining the correction value by forming the ratio of the surface area of the exposed area of the measuring field to the overall surface area of the measuring field, the control circuit including a multiplier unit for determining the dose reference value by multiplication of a given dose standard reference value by the correction value. This constitutes a simple solution for determining the correction value and the dose reference value, enabling fast exposure control.

In order to ensure that the correction value does not exceed given limit values, the means for determining the correction value in a further embodiment of the X-ray device according to the invention include a limiter unit for limiting the correction value to a predetermined minimum value and to a maximum value 1. This serves to prevent incorrect operation of the control in given border cases. The minimum value, which may amount to, for example 0.20, should apply when the primary diaphragm aperture is very small and only a very small part, for example less than 20%, of the measuring field is exposed. The maximum value of the correction value should amount to 1 and apply when the primary diaphragm aperture is so large that the entire measuring field is exposed.

The means for determining the correction value in a further embodiment of the invention include a sensor for determining the value of the aperture of the primary diaphragm device. As a result, this measuring value can be applied directly to the control circuit, for example for determining the dose reference value.

The means for determining the correction value in a further embodiment of the invention include a sensor for determining the distance between the X-ray source and the X-ray image converter.

A preferred embodiment of the X-ray device according to the invention is constructed for pulsed fluoroscopy, the means for determining the correction value being constructed so that a correction value is determined for each fluoroscopy pulse. The X-ray device according to the invention is particularly suitable for pulsed fluoroscopy since it includes a particularly simple and fast control system.

BRIEF DESCRIPTION OF THE DRAWINGS

The invention will be described in detail hereinafter with reference to the drawing. Therein.

DETAILED DESCRIPTION OF THE PREFERRED EMBODIMENTS

Figure 1:
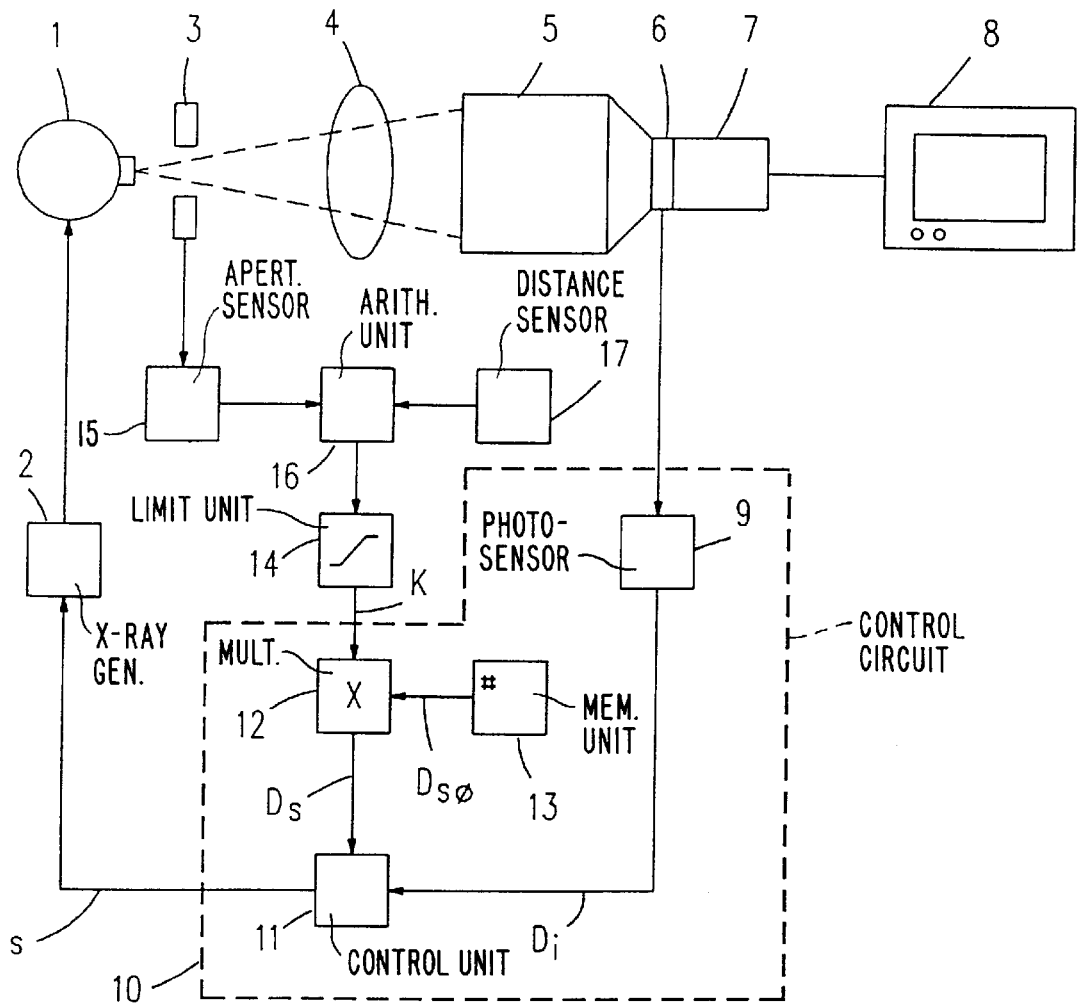
FIG. 1 shows a block diagram of an X-ray device according to the invention.

FIG. 1 shows an X-ray tube 1 which is fed by an X-ray generator 2. In front of the radiation exit opening of the X-ray tube 1 there is arranged a primary diaphragm 3 which can limit the emanating X-rays and determine the angle of aperture of the X-ray beam. Further in the beam path there is arranged an object 4 to be examined, succeeded by an X-ray image intensifier 5 which forms one unit in conjunction with an optical device 6 and a television camera 7. A monitor 8 for the display of X-ray images is connected to the television camera 7.

For automatic exposure control there is provided a control circuit 10 which generates a control signal S which is applied to the X-ray generator 2 and serves to control the tube current, the tube voltage and/or the switch-on time for the X-rays. The control circuit 10 includes a photosensor 9 whereto a part of the rays of the image formed on the exit screen of the X-ray intensifier 5 is coupled from the optical device 6, for example by means of a beam splitter or a partly transparent mirror. The photosensor 9 converts the brightness values of the optical image coupled out into a photosignal. A fixed area of the photosensor 9 then operates as a measuring field in which the dose for the exposure control is measured indirectly via the image brightness. To this end, the mean image brightness is measured by integration across the entire measuring field and a dose actual value $D_i$ is determined as an output value. This dose actual value $D_i$ is compared with a dose reference value $D_s$ in the comparison unit 11 in that, for example, these two values are subtracted one from the other. The dose reference value $D_s$ contains the information as to what the value of the exposure must be so as to ensure that the X-ray image reaches a mean density value at the area of the measuring field and hence the X-ray image has the highest possible image quality. The comparison in the comparison unit 11 yields the control signal S which, in the case where the dose reference value $D_s$ has not yet been reached, contains the information for a further increase of the X-ray dose and otherwise the information for switching off the X-rays.

In the embodiment shown, the dose reference value $D_s$ is calculated according to the invention by multiplication of a dose standard reference value $D_{s0}$ by a correction value K in the multiplier unit 12. The dose standard reference value $D_{s0}$ is supplied by a memory unit 13 in which dose standard reference values $D_{s0}$ are stored for different image intensifier formats, dose levels selected by the user, different examination modes and different pulse rates (in the case of pulsed fluoroscopy).

The calculation of the correction value K involves a number of factors. A sensor 15 determines the value of the aperture of the primary diaphragm device 3 and the distance between the X-ray source 1 and the X-ray image intensifier 5 is determined by means of a sensor 17. These values are applied to the arithmetic unit 16. The arithmetic unit 16 also stores the information concerning the dimensions of the measuring field of the photosensor 9 and also concerning the position of the measuring field relative to the exit image of the X-ray intensifier 5.

On the basis of these values, the arithmetic unit 16 determines the dimensions of the part of the surface of the measuring field which is exposed and not masked by the shutters of the primary diaphragm device 3. By the exposed (non-masked) part of the measuring field is meant that X-rays are incident at the area of the entrance screen of the X-ray image intensifier 5, associated with the exposed area of the selected measuring field, and that image brightness is produced therein. Analogously, by a non-exposed (masked) area of the measuring field is meant that no X-rays are incident in the associated area of the entrance screen of the X-ray image intensifier, because of the very small aperture of the primary diaphragm device 3, and hence no image brightness is generated either. The dimensions of the exposed area of the measuring field varies in dependence on the position and the dimensions of the measuring field and on the value of the aperture of the primary diaphragm device 3.

Figure 2:
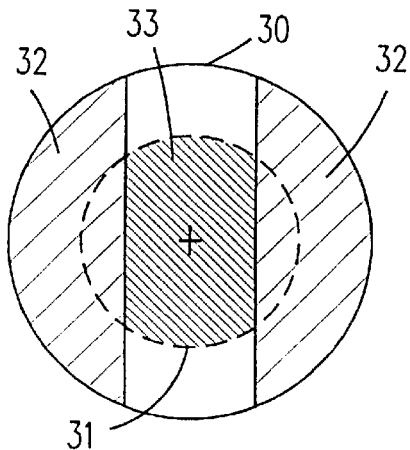
FIG. 2 shows the detector surface in order to illustrate the calculation of the correction value.

This will be illustrated again on the basis of FIG. 2. The reference numeral 30 denotes the surface of a circular photosensor. The area 31, enclosed by a dashed line, forms the measuring field which amounts to approximately 50% of the overall image surface area of the photosensor 3 in the case shown. The reference numeral 32 denotes the surface areas which are masked by the primary diaphragm shutters because of the small aperture of the primary diaphragm device 3. Thus, the areas denoted by the reference 32 are not exposed. Exposure takes place only in the (shaded) part of the surface area of the measuring field 31 which is denoted by the reference numeral 33 and the X-ray dose measured in this part by averaging should have an effect on the exposure control.

The arithmetic unit 16 calculates the correction value K from the ratio of the non-masked surface 33 to the overall surface 31 of the measuring field; this would result in a value of K of approximately 0.75 for the case shown in FIG. 2. However, because the dimensions of the non-masked surface 33 of the measuring field cannot be measured directly, the values of the primary diaphragm aperture and the distance between the X-ray source and the X-ray image converter, applied to the arithmetic unit, are used for the quasi-indirect calculation of the non-masked surface area 33.

Subsequently, a limit unit 14 limits the correction value K to a minimum value should, from a mathematical point of view, a value were obtained for K which is smaller than the minimum value, or sets the value K to the value one for the case where the entire measuring field 31 is exposed. Values of K lying between the minimum value and the value one remain unchanged.

Subsequently, in the multiplier unit 12 the correction value K is multiplied by the dose standard reference value $D_{s0}$, yielding the dose reference value $D_s$. The dose standard reference value $D_{s0}$ is thus reduced for the case of partial masking of the measuring field 31. The control signal S is thus prevented from unduly containing the information that the X-ray dose should be increased because the mean density value has not yet been reached, as would be the case for customary exposure controls; the X-rays are now switched off already when a mean density value is reached in the exposed area of the measuring field. Thus, the invention prevents overexposure of the X-ray images and hence loss of important image information. The invention also offers the advantage that the patient is not exposed to a dose which is unnecessarily high because of non-optimum control.

The X-ray device according to the invention could also be constructed so that, instead of a reduction of the dose standard reference value, the dose actual value is appropriately increased by means of the correction value in the case of partial masking of the measuring field.

Instead of a beam splitter and a photosensor for coupling out a part of the radiation and for measurement of the exposure, other known sensors are also feasible, for example an ionization chamber between the object 4 to be examined and the X-ray image intensifier 5, or a semiconductor radiation receiver. Instead of an X-ray image intensifier, the optical device and the television camera, a customary film cassette could then also be used as the X-ray image converter.

Special X-ray devices are also provided with means for varying the dimensions of the measuring field. In order to carry out the invention, such X-ray devices should also be provided with means which feed the arithmetic unit (16) with the information concerning the dimensions of the instantaneous measuring field, for example a measuring field sensor. On the other hand, the sensor 17 can be omitted in X-ray devices in which the distance between the X-ray source and the X-ray image converter cannot be varied, for example an X-ray apparatus provided with a C-arm.

The use of the invention is not limited to special X-ray devices or modes of operation. The invention can be particularly advantageously used, however, for pulsed fluoroscopy since the control according to the invention is very fast and simple and hence a control signal S can be determined for each fluoroscopy pulse.

All references cited herein, as well as the priority document German Patent Application 19702739.3 filed Jan. 27, 1997, are incorporated herein by reference in their entirety and for all purposes to the same extent as if each individual publication or patent application was specifically and individually indicated to be incorporated by reference in its entirety for al purposes.

We claim:

1. An X-ray device constructed for pulsed fluoroscopy, including:
   an X-ray source for emitting an X-ray beam,
   an X-ray image converter for detecting X-rays and for forming an X-ray image,
   a primary diaphragm device which, in order to limit the X-ray beam, is arranged between the X-ray source and an object to be examined, and
   a control circuit for automatic exposure control by the switching off of the X-ray source when a predetermined X-ray dose has been reached, the control circuit including a detector with at least one measuring field for measuring the X-ray dose rate, and
   means for determining a correction value which is dependent on the dimensions of the exposed area f the measuring field, the correction value for influencing the control circuit in such a manner that the X-ray dose remains substantially the same even when parts of the measuring field are not exposed.

2. An X-ray device as claimed in claim 1, characterized in that the control circuit includes means for determining a dose actual value, a dose reference value and a control signal by comparison of the dose actual value with the dose reference value for controlling the X-ray source.

3. An X-ray device as claimed in claim 1, characterized in that the means for determining the correction value includes an arithmetic unit for determining the correction value by forming the ratio of the surface area of the exposed area of the measuring field to the overall surface area of the measuring field, and that the control circuit includes a multiplier unit for determining the dose reference value by multiplication of a given dose standard reference value by the correction value.

4. An X-ray device as claimed in claim 1, characterized in that the means for determining the correction value includes a limiter unit for limiting the correction value to a predetermined minimum value and to a maximum value of 1.

5. An X-ray device as claimed in claim 1, characterized in that the means for determining the correction value includes a sensor for determining the value of the aperture of the primary diaphragm device.

6. An X-ray device as claimed in claim 1, characterized in that the means for determining the correction value includes a sensor for determining the distance between the X-ray source and the X-ray image converter.

7. An X-ray device as claimed in claim 1, characterized in that the X-ray device is constructed for pulsed fluoroscopy, and that the means for determining the correction value is constructed so that a correction value is determined for each fluoroscopy pulse.

8. An X-ray device as claimed in claim 2, characterized in that the means for determining the correction value includes an arithmetic unit for determining the correction value by forming the ratio of the surface area of the exposed area of the measuring field to the overall surface area of the measuring field, and that the control circuit includes a multiplier unit for determining the dose reference value by multiplication of a given dose standard reference value by the correction value.

9. An X-ray device as claimed in claim 2, characterized in that the means for determining the correction value includes a limiter unit for limiting the correction value to a predetermined minimum value and to a maximum value of 1.

10. An X-ray device as claimed in claim 3, characterized in that the means for determining the correction value includes a limiter unit for limiting the correction value to a predetermined minimum value and to a maximum value of 1.

11. An X-ray device as claimed in claim 8, characterized in that the means for determining the correction value includes a limiter unit for limiting the correction value to a predetermined minimum value and to a maximum value of 1.

12. An X-ray device as claimed in claim 2, characterized in that the means for determining the correction value includes a sensor for determining the value of the aperture of the primary diaphragm device.

13. An X-ray device as claimed in claim 3, characterized in that the means for determining the correction value includes a sensor for determining the value of the aperture of the primary diaphragm device.

14. An X-ray device as claimed in claim 8, characterized in that the means for determining the correction value includes a sensor for determining the value of the aperture of the primary diaphragm device.

15. An X-ray device as claimed in claim 4, characterized in that the means for determining the correction value includes a sensor for determining the value of the aperture of the primary diaphragm device.

16. An X-ray device as claimed in claim 9, characterized in that the means for determining the correction value includes a sensor for determining the value of the aperture of the primary diaphragm device.

17. An X-ray device as claimed in claim 10, characterized in that the means for determining the correction value includes a sensor for determining the value of the aperture of the primary diaphragm device.

18. An X-ray device as claimed in claim 11, characterized in that the means for determining the correction value includes a sensor for determining the value of the aperture of the primary diaphragm device.

19. An X-ray device as claimed in claim 2, characterized in that the means for determining the correction value includes a sensor for determining the distance between the X-ray source and the X-ray image converter.

20. An X-ray device as claimed in claim 3, characterized in that the means for determining the correction value includes a sensor for determining the distance between the X-ray source and the X-ray image converter.

* * * * *